(12) United States Patent
Viswanathan

(10) Patent No.: US 7,623,736 B2
(45) Date of Patent: Nov. 24, 2009

(54) REGISTRATION OF THREE DIMENSIONAL IMAGE DATA WITH PATIENT IN A PROJECTION IMAGING SYSTEM

(75) Inventor: Raju R. Viswanathan, St. Louis, MO (US)

(73) Assignee: Stereotaxis, Inc., St. Louis, MO (US)

(*) Notice: Subject to any disclaimer, the term of this patent is extended or adjusted under 35 U.S.C. 154(b) by 654 days.

(21) Appl. No.: 11/429,666

(22) Filed: May 5, 2006

(65) Prior Publication Data

US 2006/0269165 A1 Nov. 30, 2006

Related U.S. Application Data

(60) Provisional application No. 60/686,371, filed on Jun. 1, 2005, provisional application No. 60/678,322, filed on May 6, 2005.

(51) Int. Cl.
*G06K 9/00* (2006.01)
(52) U.S. Cl. .................. 382/293; 382/103; 382/106; 382/108; 382/109; 382/181; 382/190; 382/199; 382/201; 382/203; 382/204; 382/209; 382/213; 382/217; 382/295; 382/298; 348/144
(58) Field of Classification Search .......... 382/293, 382/103, 106, 108, 109, 181, 190, 199, 213, 382/209, 204, 203, 201, 217, 295, 298, 299; 348/144; 364/420, 525, 456
See application file for complete search history.

(56) References Cited

U.S. PATENT DOCUMENTS

| | | | | |
|---|---|---|---|---|
| 6,084,989 | A * | 7/2000 | Eppler | 382/293 |
| 7,358,732 | B2 * | 4/2008 | Van Der Kouwe et al. | 324/309 |
| 2002/0018588 | A1 * | 2/2002 | Kusch | 382/131 |

FOREIGN PATENT DOCUMENTS

WO WO2005/092198 * 6/2005

OTHER PUBLICATIONS

Tang T.S.Y (Fiducial Registration from a Single X-Ray Image:A New Technique for Fluoroscopic Guidance and Radiotherapy); pp. 502-511; May 2000.*

* cited by examiner

*Primary Examiner*—Vikkram Bali
*Assistant Examiner*—Nancy Bitar
(74) *Attorney, Agent, or Firm*—Harness, Dickey & Pierce, P.L.C.

(57) ABSTRACT

A method for determining a translation of a three-dimensional pre-operative image data set to obtain a registration of the three-dimensional image data with a patient positioned in a projection imaging system. In one embodiment the user identifies an initial three-dimensional organ center from projections and extreme contour landmark points of the object on a set of projections. A set of contour points for the image object in each of a plurality of three-dimensional cross-section planes; is obtained and the points projecting nearest to the user-identified landmark points are selected. A three-dimensional grid having a predetermined number of intervals at a predetermined interval spacing centered at the user-identified organ center is defined. The three-dimensional image data contour points as centered onto each grid point are projected for evaluation and selection of the grid point leading to contour points projecting nearest to the user-identified landmark points. This selection leads to the iterative definition of a series of improved estimated three-dimensional organ centers, and associated translation vectors. Registration of a three dimensional image data to the patient positioned in a projection imaging system will allow, among other things, overlay of a visual representation of a pre-operative image object onto a projection image plane that can serve as a visual tool and a surgical navigation aid. In particular, the position and orientation of a medical device can be shown with respect to the three-dimensional image data and thus enable quicker, safer, and less invasive navigation of the medical device to and within an organ of interest.

13 Claims, 7 Drawing Sheets

Medical device in projection x-ray image 3D visualization of medical device within 3D organ

REGISTRATION OF THREE DIMENSIONAL IMAGE DATA WITH PATIENT IN A PROJECTION IMAGING SYSTEM

CROSS-REFERENCE TO RELATED APPLICATIONS

This application claims the benefit of U.S. Provisional Patent Application Ser. No. 60/686,371, filed Jun. 1, 2005, which relates to U.S. Provisional Patent Application Ser. No. 60/678,322, filed May 6, 2005. The entire disclosures of the above applications are incorporated herein by reference.

FIELD OF THE INVENTION

This invention relates to registration of previously acquired three dimensional image data with respect to a subject body positioned in a projection imaging system, and more particularly to a method of estimating a translation vector that brings the three-dimensional data set in alignment with the subject body under examination by the projection imaging system.

BACKGROUND OF THE INVENTION

Interventional medicine is the collection of medical procedures in which access to the site of treatment is made by navigation through one of the subject's blood vessels, body cavities or lumens. Interventional medicine technologies have been applied to manipulation of medical instruments such as guide wires and catheters which contact tissues during surgical navigation procedures, making these procedures more precise, repeatable and less dependent on the device manipulation skills of the physician. Some presently available interventional medical systems for directing the distal tip of a medical device from the device proximal end use computer-assisted navigation and a display means for providing an image of the medical device within the anatomy, along with anatomical images obtained previously from a separate imaging apparatus. Such systems can display a projection of the medical device being navigated to a target destination obtained from a projection imaging system such as a Fluoroscopy (X-ray) imaging system, and can also provide a three-dimensional rendition of blood vessels and tissues obtained for example from a prior volumetric imaging examination such as a Computed Tomography (CT) examination; the surgical navigation being effected through means such as remote control of the orientation of the distal tip and proximal advance of the medical device.

In some cases, it may be difficult for a physician to become or remain oriented in a three dimensional setting using a display of a single-plane image projection. Enhancement or augmentation of the single-plane projection image may be required to aid the physician in visualizing the relative position and orientation of the medical device with respect to three-dimensional (3D) tissue surfaces and organs in the body. A method is therefore desired for enhancing a display image of the medical device and anatomical surfaces to include three-dimensional images of surfaces and organs in the body.

SUMMARY OF THE INVENTION

The present invention relates to a method for determining a translation of a three-dimensional pre-operative image data set (acquired previously by for example a 3D tomographic examination of a subject body) to register the three-dimensional image data with the subject body as positioned in a projection imaging system such as an X-ray imaging system. In one preferred embodiment of the present invention, the method comprises the following steps:

1) The user identifies a three-dimensional center point of the object or organ for which 3D data are available relative to the projection imaging system as an initial estimate for the 3D organ center;
2) The user selects at least two extreme opposing landmark points on the object projection(s) from at least one projection image plane to serve in the computation of a registration figure-of-merit (FOM); these selections define the projection set (one projection for each landmark point);
3) Defining a plurality of 3D cross-section planes with respect to the 3D data, and automatically obtaining by segmentation of the 3D image data a set of contour points for a plurality of lines on each of the plurality of cross-section planes;
4) Defining a plurality of 3D grid points for an initial set of grid parameters, and centering the 3D grid on the initial estimate of the 3D organ center;
5) For each of the projections in the projection set, performing a projection of every contour point for a first subset of the cross-section plane set obtained in step four, and selecting from the cross-section plane subset the extreme cross-section plane with the contour point projecting nearest to the user-identified landmark point, and retaining the distance from the projection of that extreme contour point to the identified landmark projection point as an additive component to the FOM;
6) Defining a refined set of sampling parameters for the 3D volume cross-section planes, and an associated second subset of the cross-section plane set defined in step four, the second subset containing planes in the neighborhood of and nearest to the extreme plane identified in step five, and iterating over step five.
7) For the 3D grid point under consideration calculating the FOM as the sum of the distances between the projections of the extreme points identified in step six and the corresponding user-identified landmark points;
8) Iterating steps five through seven over each point of the 3D grid of step three by translating the 3D data so that its center corresponds at each iteration with the selected 3D grid point; and selecting as the new 3D organ center estimate the grid point that minimizes the FOM;
9) Iterating step eight over a series of 3D grids defining successively finer samplings of the 3D volume in a neighborhood of the 3D organ center estimate obtained in step eight, and obtaining a final 3D organ center estimate from which to calculate a translation vector.

As a result of performing steps one through nine, the method enables registration of a three-dimensional image of an organ to a patient positioned in a projection imaging system, for suitable overlay of the 3D data to the image projection and resulting ease in navigation of a medical device.

BRIEF DESCRIPTION OF THE DRAWINGS

Corresponding reference numerals indicate corresponding points throughout the several views of the drawings.

DETAILED DESCRIPTION OF THE PREFERRED EMBODIMENTS

A method is provided for determining a transformation of a three-dimensional pre-operative image data set to obtain a registration of the three-dimensional image data with a patient positioned in a projection imaging system. In one embodiment of the present invention, a 3D translation vector is estimated that places the 3D data volume in registration with the patient, as determined by registering at least two points on at least one projection obtained by imaging the patient in the projection system. As a result of the registration, it is possible to determine the location and orientation of a medical device with respect to the 3D data volume; this determination facilitates the navigation of the medical device in the patient. Registration enables shorter, more accurate and less invasive navigation to and within the organ of interest. In a typical implementation, registration may render unnecessary injection of contrast medium during the navigation.

Figure 1:
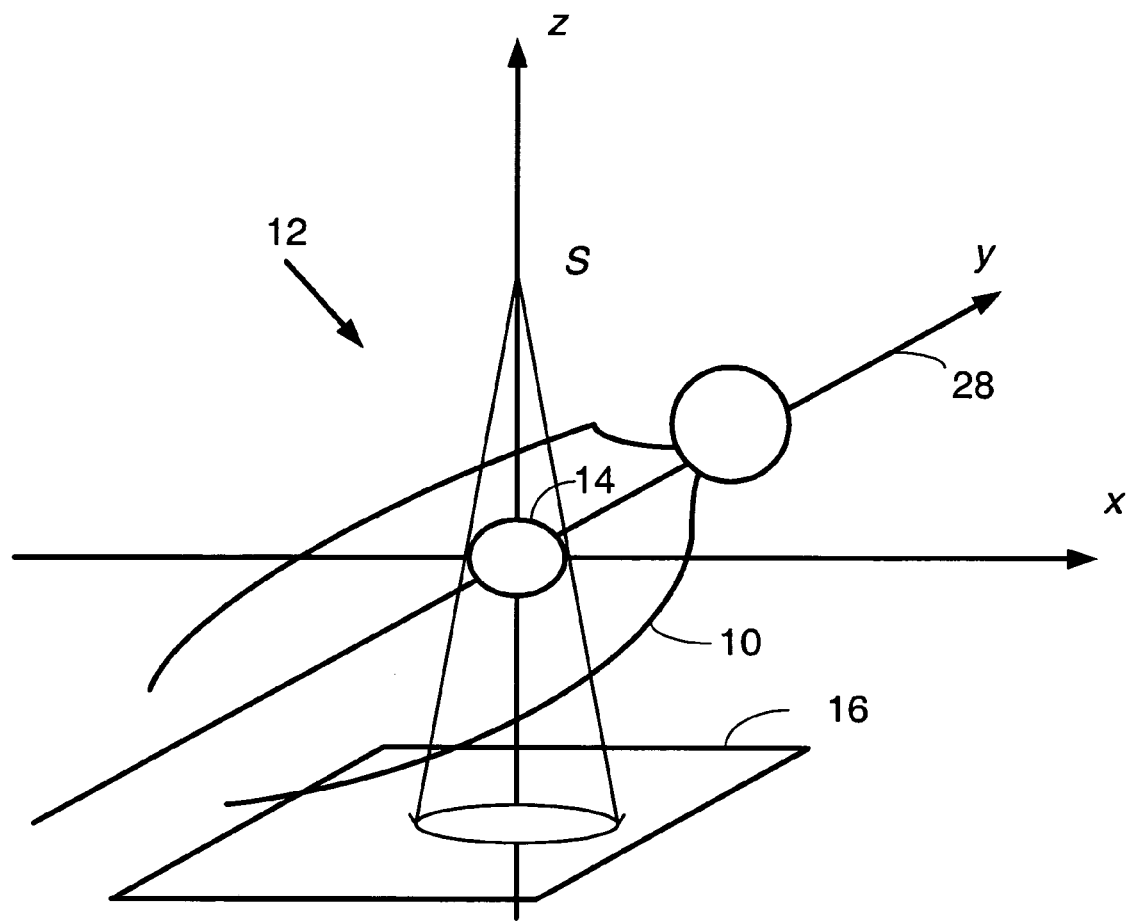
FIG. 1 shows a subject positioned into a projection imaging system and describes the geometry of the projection for an organ of interest.
Figure 2:
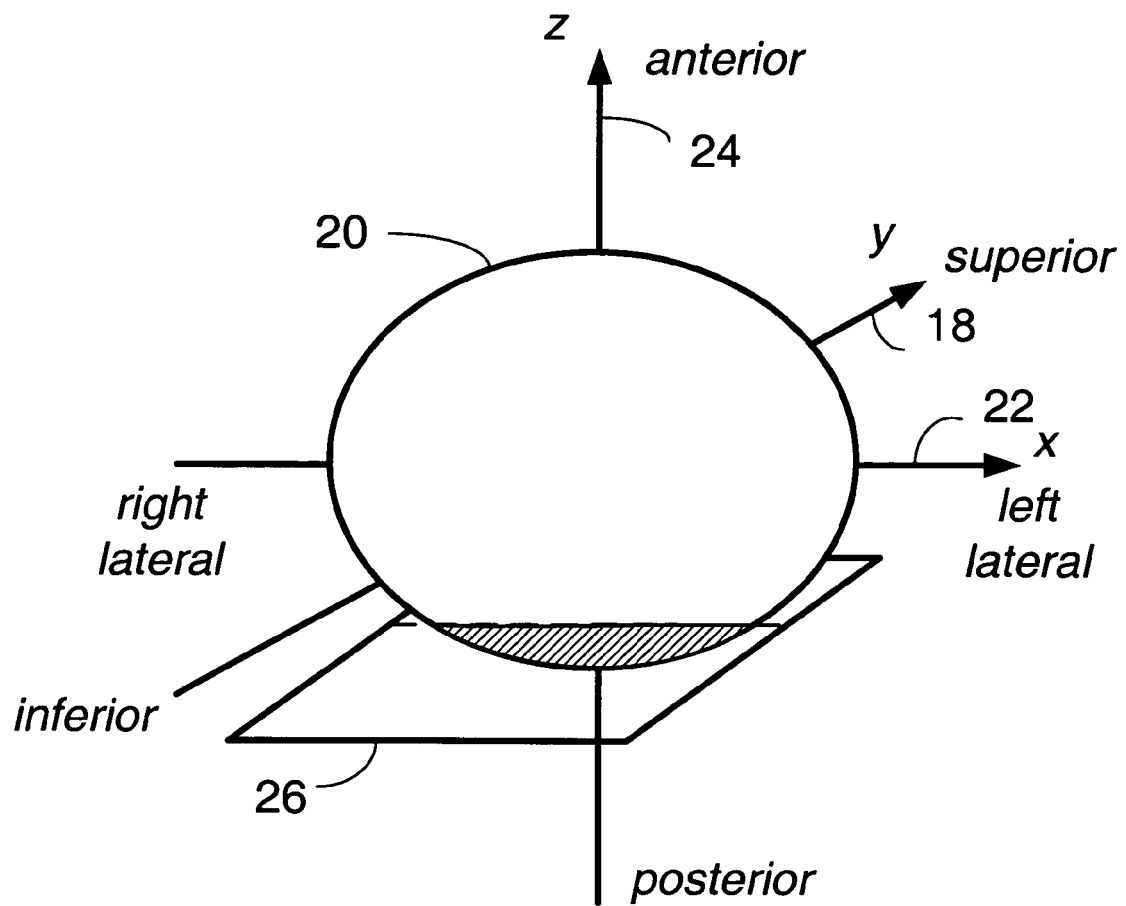
FIG. 2 illustrates a volume of data previously acquired by 3D tomographic examination of the patient and associated coordinate system.

FIG. 1 shows a subject 10 positioned within a real-time projection imaging system 12 such as an X-ray fluoroscopy imaging chain. The patient positioning is such that an organ of interest 14 projects onto the active detector 16. In a typical cardiac imaging system, the imaging chain can rotate with respect to the patient longitudinal axis y 18 to acquire projection data at a multiplicity of angles θ. The view shown in FIG. 1 corresponds to the anterior-posterior projection, also retained to define the zero of the projection imaging chain projection angle (θ=0). Data acquired previously from the patient for the organ of interest, for example through a volumetric tomographic examination, are available as a 3D volume 20, FIG. 2. In a typical cardiac examination, the patient lies supine on the examination table, and the axes x, 22, y, 18, and z, 24, respectively define the right-left lateral, inferior-superior, and posterior-anterior directions.

Figure 3:
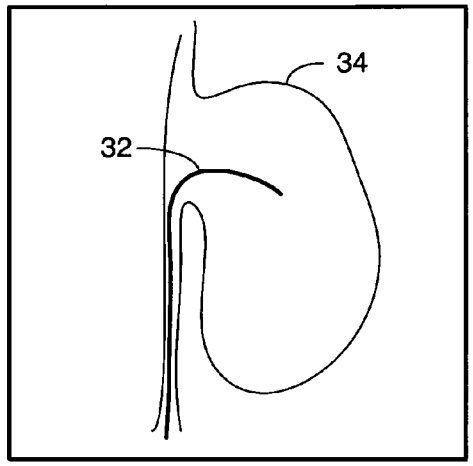
FIG. 3 presents a side-by-side display of a projection image showing a medical device in the subject body and of a volume-rendered 3D data set with the medical device shown in determined relative position and orientation within as a result of performing the registration.
Figure 3:
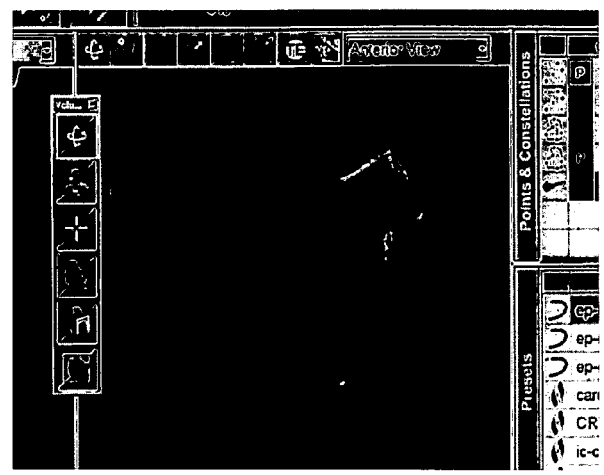

Information regarding the geometry of the projection imaging system of FIG. 1 is available. Given the orientation of the 3D data set as known from the previous data acquisition, it is possible to project the 3D data set in accordance with the geometry of the projection system at corresponding θ angles. When considering heart applications, it might be desirable to simplify the co-registration task by not taking into account in the projections of the 3D data set any data posterior to a given plane 26 at z=constant, FIG. 2. As the exact position of the patient with respect to the imaging system in the previous, tomographic examination, might differ from the patient position in the projection system, a method to estimate the translation of the 3D data set so that it is in alignment with the patient as positioned in the projection system is desirable. The availability of such a translation estimate would allow registering the projection data with the 3D data set. When performing navigation of a medical device within the subject body to and within an organ of interest, availability and display of co-registered data would allow presenting to the physician the medical device in relative position and orientation within the 3D organ (FIG. 3). Such display would greatly facilitate navigation of the medical device to and within the organ of interest, and enable shorter, safer, and less invasive interventions. FIG. 3-A shows the progression of the medical device 32 within the organ of interest 34 in projection; FIG. 3-B shows the determined relative position and orientation of the medical device with respect to the 3D organ of interest.

Figure 4:
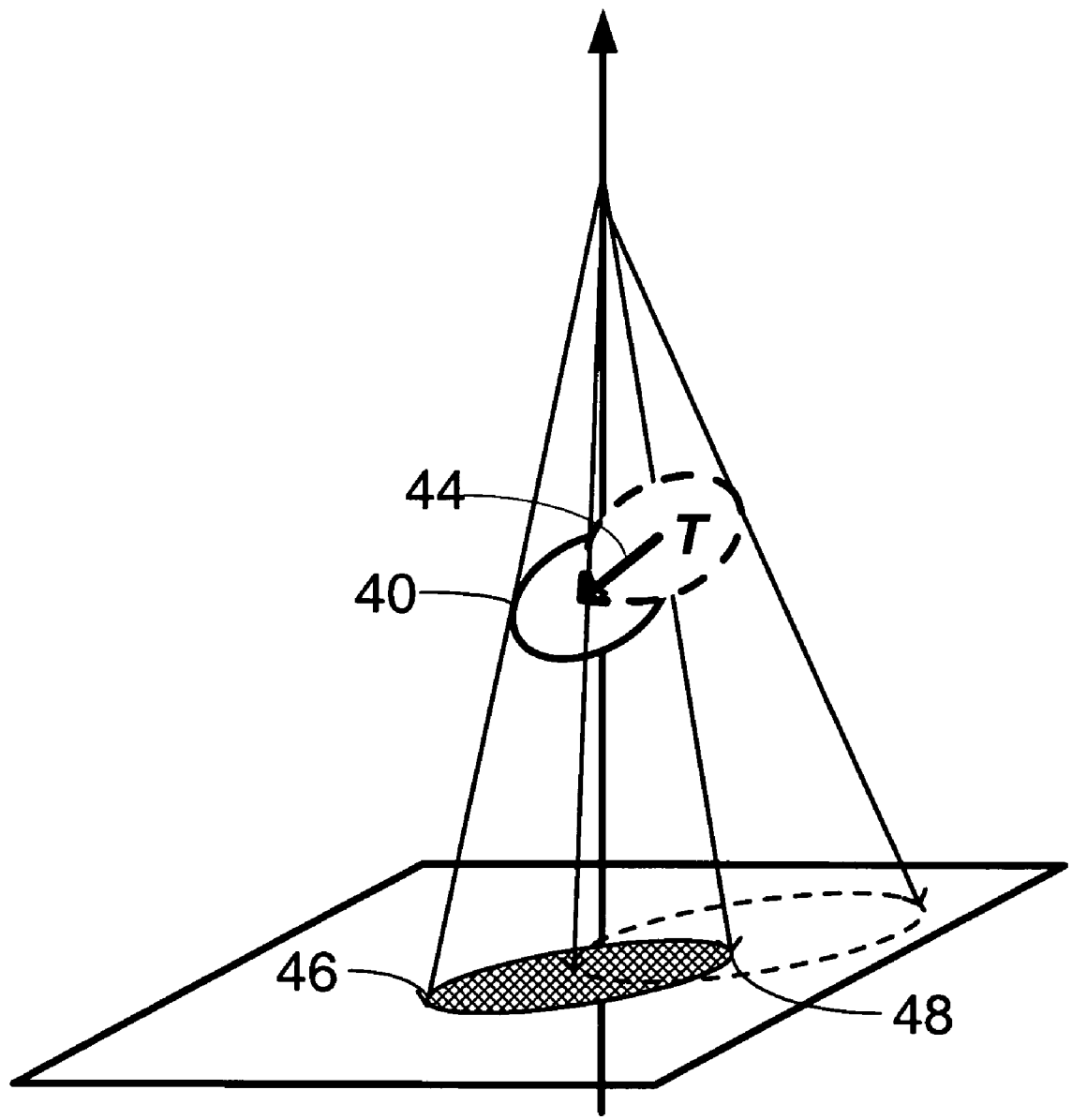
FIG. 4 illustrates how use of a set of at least two extreme points identified by the user onto at least one projection suffices to determine a translation vector T for registration of a convex volume.

FIG. 4 illustrates how the matching of extreme points, for example extreme lateral points 40 and 42, can lead to the estimation of a translation vector T 44 for a convex 3D object. Accordingly, identification by the user of two extreme landmark points 46 and 48 in at least one projection of the patient's organ of interest, and consideration of the distance from projected 3D contour points to the landmark points on the projection plane(s), leads to the definition of a figure-of-merit for registration of the 3D object to the patient as positioned in the projection system. Minimization of the figure-of-merit associated with a given translation vector effectively registers the 3D data set to the patient. This approach very significantly reduces the computational effort necessary to achieve registration. As the tomographic 3D data typically are acquired with contrast media, segmentation of the organ volume is relatively simple and can lead to a well defined organ surface. Exclusive consideration of surface or contour points also contributes to an efficient implementation of the method. Applying thresholding techniques to the 3D voxel gray levels generally suffices to effectively segment out the organ (vasculature and the heart in cardiac applications); prior gray-level smoothing of the voxel distribution can reduce the segmentation noise; and connectivity constraints can further reduce the likelihood of segmentation errors.

Figure 5:
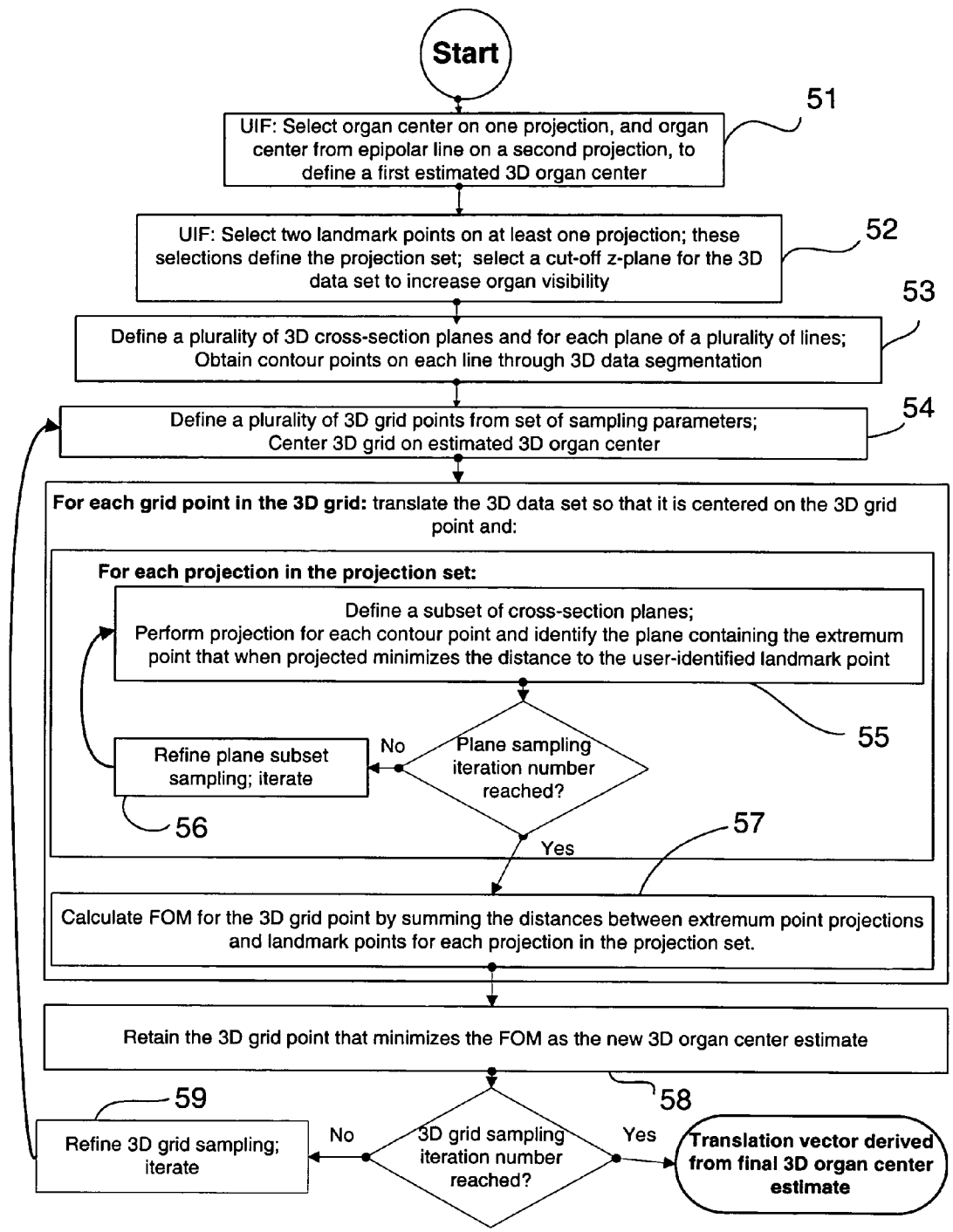
FIG. 5 presents a flow-chart diagram for one embodiment of the present invention.

FIG. 5 illustrates one embodiment of the current invention. The method proceeds in nine steps, described below.

In the first step, 51, the user identifies from two projections of the subject, the center of the organ of interest. This is achieved as follows: on a first projection, the user identifies the center of the organ contour, such as the center of the heart; the computer automatically draws from known geometry an epipolar line onto the second projection; the user then select on that line the point that best corresponds to the organ center on the second projection. An initial estimate of the organ center $C_0$ is thus determined in 3D space with respect to the projection imaging system. User identification of the organ center from the projections typically does not require injection of contrast medium. Alternatively, a default volume center could be used.

In step two, 52, the user identifies at least two contour points $(X_i, l)$ at the extreme left lateral and extreme right lateral sides of the object from at least one projection image plane. The index i identifies the laterality (i=1: left lateral; i=2: right lateral) and l is the projection index. In a typical fluoroscopic examination of the heart, the left-most lateral contour point will be best seen in the right-anterior oblique (RAO) projection, while the right-most lateral contour point will be more easily identified on the left-anterior oblique (LAO) projection. These projections at known projection angles then define the projection set. The projection set will be accessed in turn when calculating projections of the 3D data set according to the geometry of the projection system. In the following, the orientation angle of the patient in the projection system is assumed to correspond to that of the volume tomographic acquisition. Accordingly, determination of a 3D translation vector suffices to effect co-registration. Additional landmark points may also be defined by the user to either refine upon the registration result or to help in sorting local minima of the FOM function.

In step two, the user also defines the location of a plane at z=constant, or a plane of similar orientation. That plane is later used in the 3D volume data projections, to eliminate data (corresponding for example to the pulmonary vein) that would lead to the definition of erroneous organ contour points.

Figure 6:
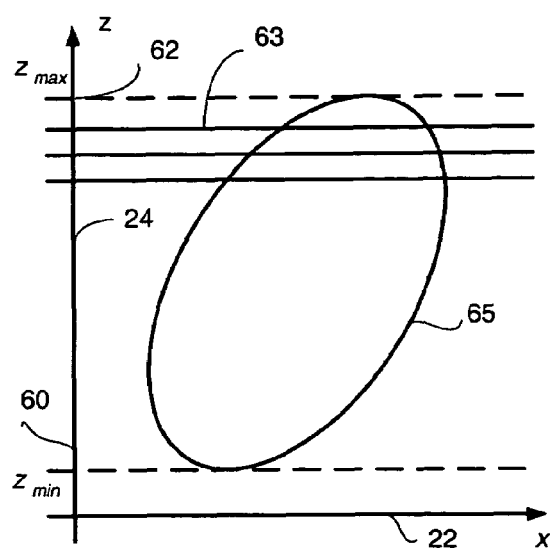
FIG. 6 presents plane samplings from the 3D volume (FIG. 6-A) and contour points identified on a set of lines through a plane sample (FIG. 6-B)
Figure 6:
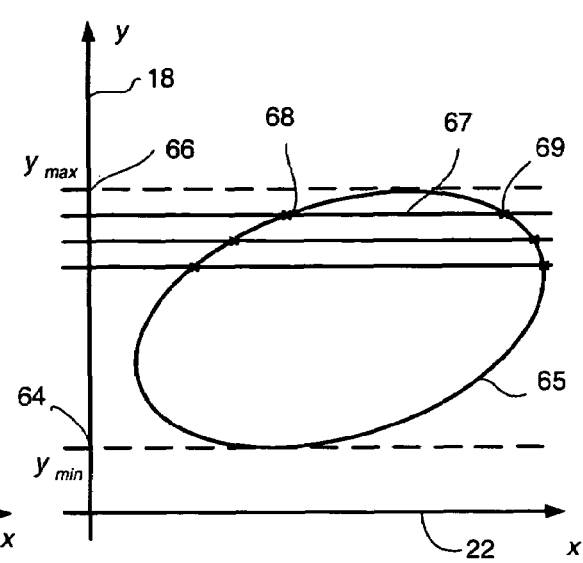

In step three, 53, a set of cross-section planes is defined for the organ of interest within a given anterior-posterior range automatically determined from the data set by segmentation. A set of planes is selected at equal increments along the z axis. For each such plane, a plurality of lines is defined within an inferior-superior range automatically determined by the data set by segmentation. A set of lines is selected at equal increments along the y axis. On each such line, one or two contour points are automatically determined by segmentation of the three-dimensional data set. These contour points correspond to the boundary of the organ of interest, such as the heart wall in cardiac examinations. In a preferred embodiment of the present invention, the most anterior and posterior points ($z_{min}$, 60, and $z_{max}$, 62, respectively) are automatically found (FIG. 6-A) and about 150 cross-section planes 63 are defined at equidistant intervals along the posterior-anterior (z) direction. In each plane, the most inferior and superior points ($y_{min}$, 64, and $y_{max}$, 66) are automatically found, and about 90 lines 67 are defined at equidistant intervals along the inferior-superior (y) direction. On each line, two contour (boundary) points 68 and 69 are automatically identified by segmentation of the 3D image data. As a result of this process, about 27,000 contour points have been defined on the 3D organ surface boundary 65. Only a subset of these contour points needs to be used in the determination of the translation vector.

Referring again to FIG. 5, in step four, 54, a first three-dimensional grid having a predetermined number of intervals at a predetermined interval spacing (grid sampling parameters) is defined. The 3D grid center is positioned at the user-identified 3D organ center. In the next steps, the registration algorithm iteratively calculates a figure-of-merit for each of the grid points. The FOM for a given grid point is obtained by centering the 3D data onto the grid point, projecting a number of evaluation contour points selected from the 3D data, and evaluating a distance to pre-selected landmark points, as further described below. In one preferred embodiment of the present invention, a 9×9×9 uniform grid with 2-cm grid spacing is defined as the initial 3D grid.

The method now proceeds iteratively over each grid point of the 3D grid identified in step four, and over each projection in the projection set. Steps five and six are included within both of these algorithm loops.

Figure 7:
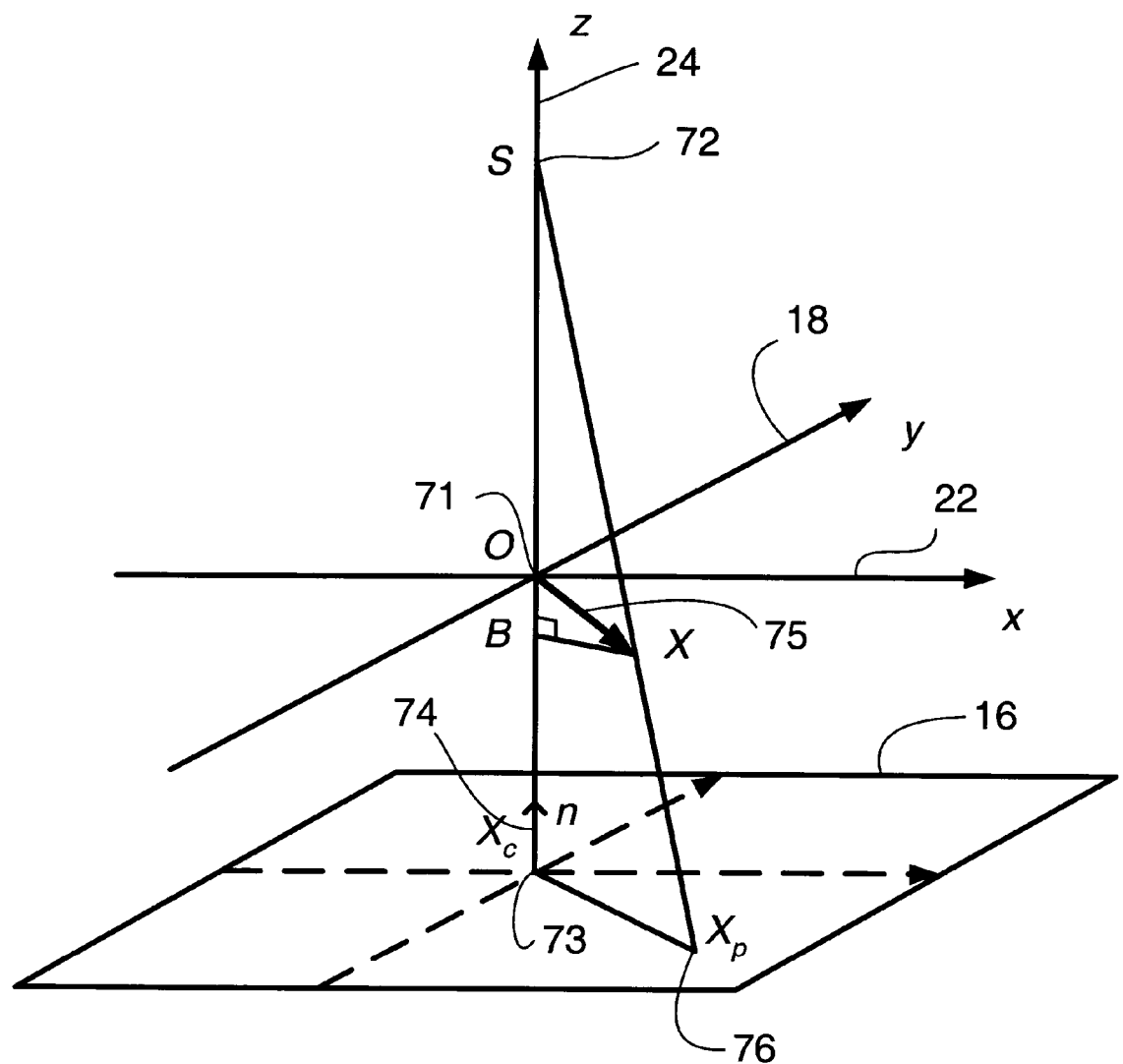
FIG. 7 details the projection geometry and projection of a given point X.

In step five, 55, the method projects every contour point on a subset of cross-section planes onto the projection image plane. The projection geometry is illustrated in FIG. 7 and further described below. The projection of these contour points establishes a set of projection points to be evaluated relative to the user-identified extreme landmark points (Xi,l) on the projection image(s). The evaluation is performed by means of a cost function, based upon the distance between the projected contour point and the user-defined landmark point associated with this projection. In a preferred embodiment of the present invention, a subset of the set of 150 planes identified in step three is defined, containing 11 planes at equidistant intervals. Each of these subset planes is indexed by j, and the contour point m(j) that minimizes that cost function is identified; for the subset of cross-section planes chosen, the plane j* that minimizes the cost function is found, and the corresponding contour point labeled m(j*).

The method further refines the above search by defining a narrower sampling of a predetermined number of neighboring section planes on each side of the cross-section plane j* selected from the prior subset. Referring to FIG. 5, in step six, 56, finer cross-section plane sampling parameters are defined, and the method iterates upon step five for the new set of cross-section planes. In a preferred embodiment of the present invention, the algorithm selects from the initial set of 150 planes defined in step three a subset of 31 planes centered around and closest to the plane indexed by j*, and determines from the refined sampling the best-fit extreme section plane with the contour point that projects closest to the user-identified landmark point. The algorithm has now identified for each user-identified landmark point $X_{i,l}$ the contour point m{j*(i,l)} that projects nearest to $X_{i,l}$.

In step seven, 57, and for a given 3D grid point, the figure-of-merit FOM is calculated by summing the distances from each of the contour points (on their respective planes j*) projections to the user-defined landmark points:

$$FOM = \sum_{i,l} \|P[X_{m\{j*(i,l)\}}] - X_{i,l}\|^2$$

where P denotes the projection operator.

In step eight, 58, each of the 3D grid points is evaluated in turn (by placing the 3D data volume center on the grid point and performing the above steps five to seven) and the grid point that is associated with the minimum FOM becomes the new 3D organ center estimate.

In step nine, 59, the method further refines the search for the closest-fit 3D organ center estimate by iteratively defining a series of succeeding grids having a predetermined number of intervals and interval spacing substantially smaller than the preceding grid spacing, and with the grid center of the next iteration located at the 3D organ center estimate obtained at the previous iteration. The method then iterates upon steps four to eight to yield a series $C_n$ of refined 3D organ center estimate. This iterative process of reducing the grid interval spacing and re-centering the grid is repeated until a grid point having a cost function of less than a predetermined value is obtained or a maximum number of iterations is reached. In a preferred embodiment of the present invention, the second grid sampling parameters are chosen to provide an interval of 0.5-cm, and the third grid provides a sampling interval of 0.625-mm.

A translation vector $T=(C_n-C_0)$ may then be written using this final 3D organ center estimate, with $C_0$ and $C_n$ representing respectively the first and last 3D organ center estimates. This translation vector enables registration of the three-dimensional image data set with the patient positioned in a projection imaging system, and dynamic overlay of a visual representation of the pre-operative image on the projection image display.

The geometry of the projection, FIG. 7, is now further detailed. Let $X_c$ represent the projection of the origin O, 71, onto the detector 16; d the source-to-image distance (SID); $b_0$ the distance between the projection vertex S 73 (X-ray source in X-ray imaging) and O; $X_{c,0}$ the detector plate center in the anterior-posterior position ($\theta$=0): $\{X^T_{c,0}=(0,0,d-b_0)\}$; and n 74 be a vector normal to the detector. The operator:

$$A = I_{3\times3} - nn^T$$

is the projection operator onto the plane orthogonal to n. Given a vector X 75 corresponding to a point in 3D space, $X_p$ 76 its projection onto the detector is then given by:

$$X_p = X_c + \frac{d}{[d - n.(X - X_c)]} \times A(X - X_c).$$

Similarly, a rotation of angle θ of the projection image chain can be represented by the matrix (LAO: θ>0; RAO: θ<0):

$$R = \begin{pmatrix} \cos\theta & 0 & \sin\theta \\ 0 & 1 & 0 \\ -\sin\theta & 0 & \cos\theta \end{pmatrix},$$

and its effect on the projection equation is described by the equations:

$$X_p = RX_l + X_c$$

With $X_l^T = (x,y,0)$ in (local) detector coordinates, $$X_l = \frac{d}{[d - n.(X - X_c)]} \times R^T A(X - X_c),$$

with $X_c = RX_{c,0}$, 73.

The advantages of the above described embodiment and improvements should be readily apparent to one skilled in the art, as to enabling the determination of a translation for use in registering a previously acquired three-dimensional image of an organ of interest with a patient positioned in a projection imaging system. Additional design considerations may be incorporated without departing from the spirit and scope of the invention. Accordingly, it is not intended that the invention be limited by the particular embodiment or form described above, but by the appended claims.

The invention claimed is:

1. A method for registration of a previously acquired three-dimensional image data set of an organ of interest in a patient, to the patient positioned in a projection imaging system, comprising the steps of:
    (a) identifying an initial three-dimensional center point estimate for the three-dimensional organ of interest from projections acquired in the projection imaging system;
    (b) identifying at least two extreme landmark points on a set of at least one projection acquired in the projection imaging system and defining a set of landmark-associated projections;
    (c) defining a plurality of cross-section planes with respect to the three-dimensional data, and automatically obtaining by segmentation of the three-dimensional image data a set of contour points for a plurality of lines on each of the plurality of cross-section planes;
    (d) defining a plurality of three-dimensional grid points for an initial set of grid parameters, and centering the three-dimensional grid on the initial estimate of the organ center obtained in step (a);
    (e) centering the three-dimensional image data set on a point of the grid defined in step (d) and for each of the projection in the projection set of step (b), performing a projection of every contour point in a first subset of the cross-section plane set obtained in step (c), and selecting from the cross-section plane subset the extreme cross-section plane with the contour point projecting nearest to the user-identified landmark point of step (b), and retaining the distance from the projection of that extreme contour point to the identified landmark projection point as an additive component to a figure-of-merit;
    (f) defining a refined set of sampling parameters for the cross-section plane set of step (c), and an associated second subset of cross-section planes in the neighborhood of the extreme plane identified in step (e), and iterating over step (e);
    (g) calculating the figure-of-merit as the sum over the projection set of step (b) of the additive figure-of-merit components of step (f);
    (h) iterating steps (e) to (g) for each grid point of the grid defined in step (d) in turn by placing the center of the three-dimensional image set on the grid point, and selecting as the new three-dimensional organ center estimate the grid point that minimizes the figure-of-merit; and
    (i) iterating step (h) over a series of three-dimensional grids replacing the grid of step (d) and defining successively finer samplings of the three-dimensional volume in a neighborhood of the three-dimensional organ center estimate obtained in step (h), and obtaining a final three-dimensional organ center estimate from which to calculate a translation vector,
whereby registration of the previously acquired three-dimensional data set of an organ of interest to the patient positioned in the projection imaging system is achieved with a degree of efficiency by applying the translation vector of step (i) to the three-dimensional data set.

2. The method of claim 1, wherein the initial organ center estimate of step (a) is obtained by the user selecting an estimate of the organ center in one projection, and then selecting an estimate of the organ center on a second projection along an epipolar line drawn automatically from knowledge of the projections geometry.

3. The method of claim 1, wherein in step (b) the user is assisted in selecting extreme landmark points by automated image processing and image segmentation tools.

4. The method of claim 1, wherein the first grid parameters of step (d) comprise a grid sampling interval in the range of 1 to 3 cm, and the grid comprises 9×9×9 points.

5. The method of claim 1, wherein in step (c) the minimum and maximum range of the organ of interest along the anterior-posterior axis is identified, and wherein a number of planes in the range 100 to 200 is retained, and the planes are equispaced within the range of interest.

6. The method of claim 1, wherein the step (c) of identifying cross-section planes also comprises the step of defining a cut-off plane to eliminate data on one side of the plane in the projections of the three-dimensional data set.

7. The method of claim 1, wherein in step (c) in each plane the organ of interest range along the inferior-superior direction is identified, and wherein a number of lines in the range 60 to 120 is retained, and the lines are equispaced within the range of interest.

8. The method of claim 1, wherein the step of defining contour points on each line of step (c) by segmentation comprises the steps of pre-filtering the gray-scale volumetric data, performing thresholding, and imposing connectivity constraints.

9. The method of claim 1, wherein the step of evaluating a distance between points in step (e) as an additive component to a figure-of-merit comprises calculating an Euclidian norm distance between the points.

10. The method of claim 1, wherein the steps of defining a first subset of cross-section planes in step (e) and defining a second subset of cross-section planes in step (f) comprises the steps of first selecting a subset of N evenly-spaced planes from the full cross-section plane set, and second of selecting the nearest M planes in the neighborhood of the extreme plane of step (e), with an equal number of planes on either side of the extreme plane, and wherein N is in the range 3 to 21 and M is in the range 7 to 51.

11. The method of claim 1, wherein the step of calculating the figure-of-merit in step (g) comprises the step of summing the Euclidian distance between the landmark points and the contour points that project closest thereto, and wherein each distance component is associated with a separate landmark point.

12. The method of claim 1, wherein the step (i) of iterating over a series of three-dimensional grids comprises the steps of defining a second grid with grid interval of X mm and a third grid with grid interval of Y mm, wherein X is in the range 2 to 8 mm, and Y is in the range 0.2 to 0.8 mm.

13. The method of claim 1, wherein the step (i) of iterating over a series of three-dimensional grids comprises the steps of defining a series of decreasing grid intervals, and iterating over the grids until either a figure-of-merit less than a given value has been obtained or a maximum number of grid iterations has been reached.

\* \* \* \* \*

UNITED STATES PATENT AND TRADEMARK OFFICE
CERTIFICATE OF CORRECTION

| | |
|---|---|
| PATENT NO. | : 7,623,736 B2 |
| APPLICATION NO. | : 11/429666 |
| DATED | : November 24, 2009 |
| INVENTOR(S) | : Raju R. Viswanathan |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 809 days.

Signed and Sealed this

Twenty-sixth Day of October, 2010

David J. Kappos
*Director of the United States Patent and Trademark Office*